United States Patent [19]
Niedrig et al.

[11] Patent Number: 5,612,453
[45] Date of Patent: Mar. 18, 1997

[54] SELECTED PEPTIDES OF THE GROUP-SPECIFIC ANTIGEN (GAG) OF HUMAN IMMUNODEFICIENCY VIRUS (HIV), THE PREPARATION AND USE THEREOF

[75] Inventors: Matthias Niedrig, Marburg; Susanne Modrow, München; Hans Wolf, Starnberg, all of Germany

[73] Assignee: Chiron Behring GmbH & Co., Marburg, Germany

[21] Appl. No.: 356,798

[22] Filed: Dec. 13, 1994

Related U.S. Application Data

[63] Continuation of Ser. No. 191,706, Feb. 4, 1994, abandoned, which is a continuation of Ser. No. 47,051, Apr. 12, 1993, abandoned, which is a continuation of Ser. No. 805,689, Dec. 12, 1991, abandoned.

[30] Foreign Application Priority Data

Dec. 14, 1990 [DE] Germany ............ 40 39 925.7

[51] Int. Cl.$^6$ ............ A61K 38/00; C07K 7/08; C07K 14/00
[52] U.S. Cl. ............ 530/327; 530/324; 530/328
[58] Field of Search ............ 530/324, 327, 530/328; 514/12, 14, 15

[56] References Cited

U.S. PATENT DOCUMENTS 4,629,783  12/1986  Cosand ............ 435/68.1

FOREIGN PATENT DOCUMENTS

| | | |
|---|---|---|
| 0193284 | 9/1986 | European Pat. Off. . |
| 0356007 | 2/1990 | European Pat. Off. . |
| WO8606414 | 11/1986 | WIPO . |
| 9007119 | 6/1990 | WIPO . |

OTHER PUBLICATIONS

Coates, Nature, vol. 326, 9 Apr. 1987, pp. 549–550.
Sternberg, et al, vol. 218, No. 2, pp. 231–237, Feb., 1987.
Palker, et al, J. Experimental Medicine, vol. 159. 1984, 1117–1131, 1984.
Mascagni, et al, Tetrahedron Letters, vol. 31, No. 32, pp. 4637–4640, 1990.
Ratner, et al, Nature vol. 313 pp. 280–284, 1985.
Human Immunodeficiency Virus–Like Particles Produced By A Vaccina Virus Expression Vector, Karacostas et al., Proc. Natl. Acad. Sci. USA, vol. 86 8964–8967 (1989).
Assembly And Release Of HIV–1 Precursor Pr55gag Virus––Like Particles From Recombinant Baculovirus–Infected Insect Cells, Gheysen et al., Cell, vol. 59, 103–112 (1989).
Role Of Capsid Precursor Processing And Myristoylation In Morphogenesis And Infectivity Of Human Immunodeficiency Virus Type 1, Goettlinger et al. Proc. Natl. Acad. Sci. USA, vol. 86, 5781–5785 (1989).
Complete Nucleotide Sequence Of The Aids Virus, HTLV–III, Ratner et al., Nature vol. 313, 277–284 (1985).
Detection Of Human Immunodeficiency Virus And Other Retroviruses In Cell Culture Supernatants By A Reverse Transcriptase Microassay, Gregersen et al., Journal of Virological Methods 19, 161–168 (1988).
Application Of Polyamide Resins To Polypeptide Synthesis: An Improved Synthesis Of –Endorphin Using Fluorenylmethoxycarbonylamino–acids, Atherton et al., J. Chem. Commun. 13, 539–540 (1978).

Primary Examiner—Douglas W. Robinson
Assistant Examiner—S. G. Marshall
Attorney, Agent, or Firm—Barbara G. McClung; Robert P. Blackburn

[57] ABSTRACT

The invention relates to preparation of selected peptides of the HIV gag protein and derivatives thereof which comprise the peptide sequence NPGLLETSEGCRQ, and which inhibit HIV.

1 Claim, 10 Drawing Sheets

SELECTED PEPTIDES OF THE GROUP-SPECIFIC ANTIGEN (GAG) OF HUMAN IMMUNODEFICIENCY VIRUS (HIV), THE PREPARATION AND USE THEREOF

This application is a continuation, of application Ser. No. 08/191,706 filed Feb. 4, 1994, abandoned, which is a continuation application of Ser. No. 08/047,051 filed Apr. 12, 1993, abandoned; which is a continuation application of Ser. No. 07/805,689 filed Dec. 12, 1991, abandoned.

BACKGROUND AND SUMMARY OF THE INVENTION

The invention relates to selected peptides of the HIV gag sequence which bring about inhibition of virus synthesis. On testing 41 sequential peptides for inhibition of HIV replication it was found that the overlapping peptides 4 and 5 with the amino-acid sequence WASRELERFAVNPGLLETSEGCRQ and NPGLLETSEGCRO-ILGQLQPSLQT from the p17 submembrane protein and the two peptides 28 and 29 with the amino-acid sequences ANPDCKTILKALGPAATLEEMMTA and AATLEEMMTAC-QGVGGPGHKA from the p24 core protein inhibit the replication of HIV ( overlapping regions are underlined in each case ) . Peptides of this or similar types which contain at least the overlapping regions are suitable as pharmaceuticals for controlling HIV infections.

The disease AIDS caused by HIV represents a great challenge to scientific research in the development of therapeutically active substances and novel vaccines. Even though research extends over the entire spectrum of possible therapeutic approaches, nevertheless only a very few substances promise the prospect of a novel successful therapy. To date the only substance with anti-HIV activity which is approved on the market is ᴿRetrovir with the active ingredient zidovudine supplied by Wellcome. This nucleotide analog, azidothymidine (AZT), very effectively inhibits in vitro and in vivo the HIV-specific reverse transcriptase but is not free of disadvantageous properties. To date there are no alternatives to AZT therapy.

Investigations of the viral structure of HIV and the part played by the various virus structural proteins in virus maturation have led to the realization that several approaches for effective inhibition of virus synthesis are offered here, the inhibition of viral protease by chemotherapeutics being only one example which is currently being looked at by various research groups. The fact that the gag sequence is one of the highly conserved regions in the HIV genome suggests that this is a very important protein for virus replication; this suggestion is supported by the small differences in sequences between different HIV isolates (see Tab. 1). The process of virus synthesis is initiated by gag protein synthesis and the required myristoylation of the gag protein. Subsequent assemblage takes place on the lipid membrane of the infected cell. Juxtapositioning of gag proteins leads to a protuberance on the cell membrane and the detachment (budding) of "particles" or immature viruses. The fact that this process takes place even when only the gag gene is inserted into the cell has been shown by investigations with recombinant gag sequences in vaccinia or baculo vectors (Karacostas et al. (1989) Human immunodeficiency virus-like particles produced by vaccinia virus expression vector. Proc. Natl. Acad. Sci. USA, Vol. 86, 8965–8967; Gheysen et al. (1989) Assembly and release of HIV-1 precursor prgag55 virus-like particles from recombinant baculovirus-infected insect cells. Cell, 59, 103–112). Other publications demonstrate that there are regions important for processing within the gag sequence. Several regions relevant for the processing have been identified by introducing specific mutations within the gag sequence (G öttlinger et al. (1990) Role of capsid precursor processing and myristoylation in morphogenesis and infectivity of human immunodeficiency virus type 1. Proc. Natl. Acad. Sci. USA, Vol. 86, 5781–5785).

However, there has been no evidence whatever that certain regions of the gag sequence code for peptides which inhibit virus synthesis by HIV.

The experiments on which the invention is based investigated 41 mutually overlapping synthetic peptides of the HIV-1 gag sequence for their inhibiting function on virus synthesis in an in vitro test. The peptides were 24 amino acids long and were synthesized in analogy to the sequence published by Ratner et al. (Complete nucleotide sequence of the AIDS virus, HTLV-III, Nature, 313, 277–284 (1985)).

These peptides were added in various concentrations (200–40 µg/ml) to freshly infected jurkat cells. Infection was carried out with 100–1000 $TCID_{50}$. The infection was analyzed by microscopic assessment and investigation of the supernatant for the content of infectious HIV. For this purpose, the cell supernatant was added to non-infected jurkat cells. After incubation for two weeks, this detector cell culture was examined for HIV under the microscope and by reverse transcriptase assay. It was found from this that there are two gag regions which exert an inhibitory effect on virus synthesis. These two regions are each represented by two peptides, the first peptide (peptide 4+5) being located inside p17, and the second (peptide 28+29) being located inside p24.

As is evident from Tab. 4, no p24 is detectable in HIV-infected cells after treatment with these peptides. The supernatant from these cell cultures contains no infectious HIV capable of infecting a control culture. FIGS. 1 and 2 report the reverse transcriptase (RT) activity of the two detector cell cultures. The four selected peptides are able very effectively to inhibit HIV synthesis in concentrations of 200–40 µg/ml. (See examples for details of the demonstration of HIV inhibition).

The effect of different concentrations of infectious virus on the course of the experiment is relatively low and is mainly reflected by the level of measured RT activity (cf. Experiment 1, FIG. 1; Experiment 2, FIG. 2). Nor do different concentrations of added peptides have a significant effect on the inhibition, which suggests that the concentration of added peptides can be even further reduced without influencing the effect. The result of the third experiment is reported in FIG. 3. The reverse transcriptase activities depicted here are as measured on the cell culture supernatant after concentration five-fold after incubation of the detector cell cultures for two weeks. This again shows the strong inhibitory effect of peptides 2, 4, 5, 9, 28 and 29 on HIV-1 synthesis. Inhibition of HIV-2 synthesis by peptides 4, 5, 28 and 29 is also very clearly evident. Nevertheless, in this case the added peptides appear to have a weaker inhibitory effect. Thus, there is no inhibition with peptides 2 and 9, while complete inhibition of virus synthesis is possible with 28 only at the 200 µg/ml dose. Cytotoxicity was found only for peptide No. 9 among all the 41 investigated peptides.

The invention accordingly relates to peptides which contain at least one of the two peptide sequences NPGLLET-SEGCRO and AATLEEMMTA and are not larger than 50 amino acids, in particular not larger than 40 amino acids, especially not larger than 30 amino acids, preferably not larger than 20 amino acids. Particularly preferred peptides contain peptides 4, 5, 28 or 29.

Another embodiment of the invention relates to peptides which contain at least one of the two peptide sequences NPGLLETSEGCRO and AATLEEMMTA, where the sequences can be truncated by up to 7 amino acids, preferably by up to 4 amino acids, at the N and/or at the C terminus but without the length falling below 6 amino acids. It is also frequently advantageous to extend the peptides according to the invention by one or more amino acids, for example cysteine, in order to achieve linkage of the peptides to one another or to a carrier.

The invention furthermore relates to derivatives of the two peptide sequences NPGLLETSEGCRQ and AATL-EEMMTA in which one or more of the following substitutions can be carried out by methods known to the person skilled in the art: asparagine by glutamine, or glutamine by asparagine, proline by hydroxyproline, leucine by isoleucine or by norleucine, glutamic acid by aspartic acid, threonine by serine or serine by threonine, cysteine by serine, arginine by lysine, alanine by glycine and/or methionine by norleucine. Replacement of a natural amino acid by an unnatural amino acid such as, for example, hydroxyproline or norleucine is preferred. This makes it possible to prevent endogenous proteases cleaving the derivative, which generally results in an increase in the half-life. It is also possible for the derivatives to have improved solubility and/or better absorption than the two peptide sequences according to the invention.

The invention further relates to the preparation by protein chemistry or genetic manipulation and to the use of the peptides according to the invention as pharmaceuticals.

DETAILED DESCRIPTION OF THE INVENTION

The peptides according to the invention are preferably prepared by protein chemistry, for example as described by BARANI, G. and MERRIFIELD, R. B. in "The Peptides, Analysis, Synthesis and Biology", Vol. 2, Academic Press 1980, Ed. Erhard Gross, Johannes Meienhofer.

The invention is explained in detail in the examples and contained in the patent claims.

EXAMPLE 1

General Principles

Cells. Permanently growing T lymphocytes (Jurkat or H9 cells) were used for the in vitro experiments. The medium used was conventional RPMI 1640 with 10% FCS, 2% NaHCO$_3$ (5% strength), 1% penicillin/streptavidin solution and 2 mg/l Polybrene. The experiments were carried out either in 96-well microtiter plates (Nunc) or in 24-well plates (Nunc).

Viruses. HIV-1 virus strain HTLV-IIIB and HIV-2 strain ROD were used.

Peptide synthesis and peptide purification. The peptides were prepared according to the HIV-1 sequence published by Ratner et al. (1985) in an automatic synthesizer (Milligen 9050, Milligen GmbH, Eschborn, FRG) using Fmoc-protected amino acids (Bachem AG, Heidelberg, FRG) (Atherton et al. (1978): A mild procedure for solid phase peptide synthesis; Use of Fluorenylmethyloxycarbonyl amino acids: J. Chem. Soc. Chem. Commun. 13, 539–540). The support material used in each case was $^R$Tentagel resin with acid-stable AM linker (Rapp-Polymere, Tübingen, FRG). The amino acids were each dissolved in DMF before the coupling and converted into hydroxybenzotriazole-activated esters. Rapid synthesis cycles with a 10-minute reaction time were employed for the coupling. The Fmoc group was subsequently eliminated with 20% piperidine. This reaction was checked for completeness by fluorimetry.

After the synthesis was complete, the resin with the protected peptide was suspended in 50% TFA/DCM. Added as scavengers were 1% anisole, 1% m-cresol, 1% phenol and, if Trp was present in the particular sequence, 5% mercaptoethanol. The bonding to the resin and the Trt and tBoc protective groups were eliminated in an incubation time of 4 hours at room temperature under argon protective gas. To remove the Mtr protective group from Arg, the eliminated peptide was separated from the resin, the solvent was stripped off in a rotary evaporator, and the remaining solid substance was incubated in 100% including the usual scavengers (see above) overnight. The deprotected peptides were, after the solvent had been stripped off, dissolved in 50% acetic acid, precipitated in a large volume of ice-cold t-butyl ethyl ether, washed several times and lyophilized. The dried crude substance was taken up in 1.5% ammonium bicarbonate. Insoluble constituents were removed by filtration. The filtrate was again dried. The peptides were purified on a semipreparative Propep reversed phase HPLC column (C$_2$/C$_{18}$ copolymer, Pharmacia/LKB, Freiburg, FRG), normally employing for the elution gradients of 0–70% acetonitrile in 0.1% TFA gassed with helium. The sequences of the purified peptides were checked in a gas-phase sequencer (Applied Biosystems, Westerstadt, FRG). The peptides employed correspond to the amino-acid sequences depicted in FIGS. 6A and 6B. It is, of course, also possible to prepare the abovementioned peptides by genetic manipulation, for example as suitable fusion proteins in pro- or eukaryotic cell systems.

Reverse transcriptase assay. The microassay for detecting viral reverse transcriptase was carried out by the method of Gregersen et al. (Gregersen et al. (1988) Detection of human immunodeficiency virus and other retroviruses in cell culture supernatants by a reverse transcriptase microassay. J. Virol. Methods 19, 161–168). Cell culture supernatants were concentrated five-fold by PEG precipitation. Positive controls (VC) were supernatants of untreated infected cell cultures, and negative controls (NC) were cell culture supernatants from uninfected cells. The value measured for the NC was doubled and used as value for excluding negative cells. To improve clarity, the measured RT values are reported in logarithmic presentation (see also FIG. 1, 2, 3).

EXAMPLE 2

Demonstration of the Inhibition of HIV Synthesis

The design of the experiment is shown diagrammatically in FIG 7. In each case two experiments on the inhibition of HIV synthesis were carried out with all 41 available peptides.

In the first experiment, 50 µl of 1×10$^6$ jurkat cells/ml were pipetted into each well of 96-well plates, and each was infected with 50 µl (1000 TCID$_{50}$) HTLV-IIIB. The gag peptide concentration was adjusted to 200 µg/ml or 40

μg/ml. After one week, 100 μl of supernatant were removed and any cells still present were removed by centrifugation. Then 80 μl of supernatant were placed on an uninfected jurkat cell culture. Viral antigen was detected in the infected cells by immunolabeling after a Western blot. For this, the cells remaining after the inhibition experiment were taken up in 2×SDS-PAGE sample buffer and fractionated in a 14% PAG. The fractionated proteins were then blotted onto a nitrocellulose membrane and incubated with an anti-p24 HIV-1 monoclonal antibody to detect viral proteins. The specific staining took place via a second anti-mouse antibody with coupled alkaline phosphatase. Infectious HIV in the supernatant of the peptide-treated cells was analyzed by the reverse transcriptase assay.

The second experiment was carried out in analogy to the first experimental approach with a lower concentration of infectious units (100 $TCID_{50}$). The analyses for infectious virus in the cell culture supernatant and HIV protein in the infected cell cultures were carried out in analogy to the first experiment. In a third experimental approach, selected peptides (2, 4, 5, 9, 28, 29) which exerted an inhibitory effect on HIV-1 synthesis were tested under the same conditions for their inhibitory effect on HIV-2. H9 cells were infected with 100 $TCID_{50}$ HIV-2 for this experiment. The analysis of the infection was carried out in analogy to the two preceding experiments.

In the first two experiments two regions inside the gag sequence, each of which are represented by two overlapping peptides, which exert an inhibitory effect on HIV synthesis were identified. Peptides 4 and 5 are located inside the p17 protein sequence, while 28 and 29 are located inside the p24 protein sequence.

In FIGS. 4A to 5B comparing various HIV gag protein sequences, the regions represented by peptides 4, 5 and 28, 29 are marked by boxes. FIGS. 6A–6B lists the amino-acid sequence of the 41 mutually overlapping sequences.

Tab. Inhibition of HIV synthesis with gag peptides. Evaluation of the p24 detection in HIV-infected cells after peptide treatment two weeks after infection. Cells from the initial plate were mixed with 2×sample buffer and fractionated in a 14% PAG. Blotting onto nitrocellulose was followed by detection of HIV protein by specific anti-p24 MAbs. –=no reaction detectable, (+)=slight reaction detectable, +=good positive reaction detectable, ++=strong reaction detectable.

TAB. 1

Figure 1:
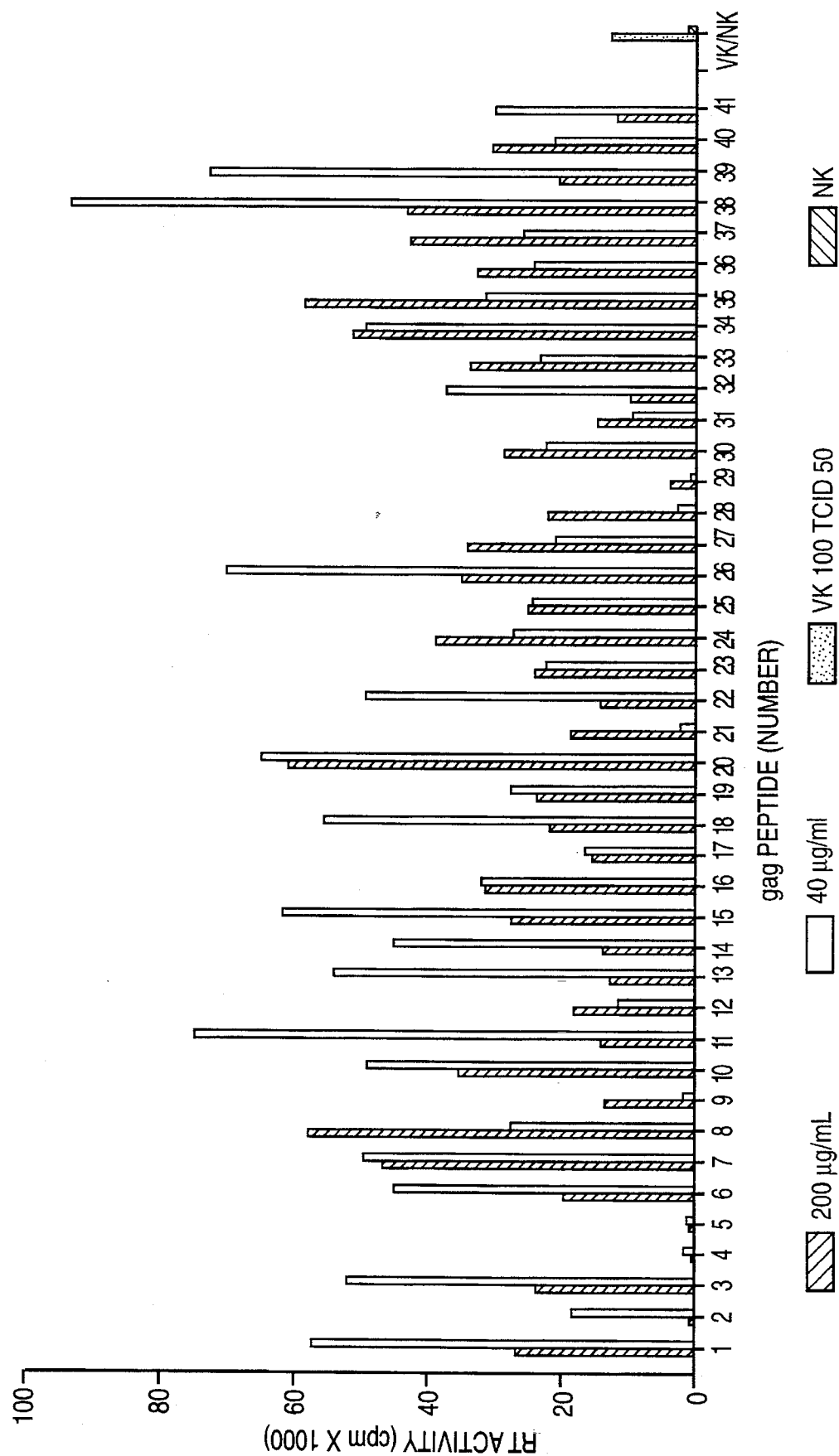
FIG. 1: Inhibition of HIV virus synthesis by gag peptides (Experiment 1). 1000 $TCID_{50}$ HIV-1 were employed for infecting the jurkat cells. Reverse transcriptase activity measured in cpm in the cell culture supernatant from the detector cell culture. The supernatant was concentrated five-fold by PEG precipitation. VC=virus control; NC=negative control. Twice the NC value was used to exclude negative cell cultures. To improve clarity, the RT values are reported in the figure in logarithmic presentation.
Figure 2:
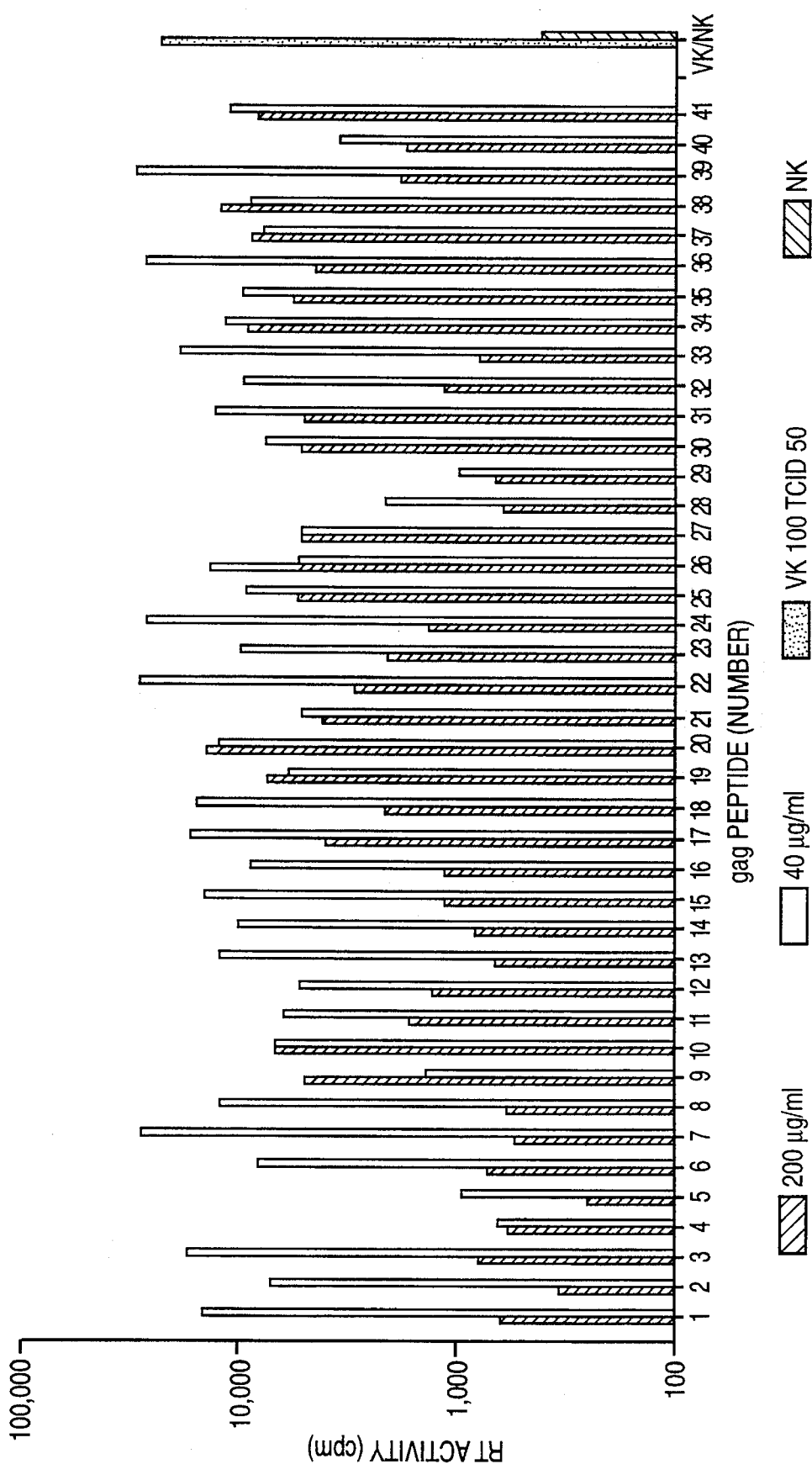
FIG. 2 Inhibition of HIV synthesis by gag peptides (Experiment 2). 100 $TCID_{50}$ HIV-1 were employed to infect the jurkat cells. Reverse transcriptase activity measured in cpm in the cell culture supernatant from the detector cell culture. The supernatant was concentrated five-fold by PEG precipitation. VC=virus control; NC=negative control. Twice the NC value was used to exclude negative cell cultures. To improve clarity, the RT values are reported in the figure in logarithmic presentation.
Figure 3:
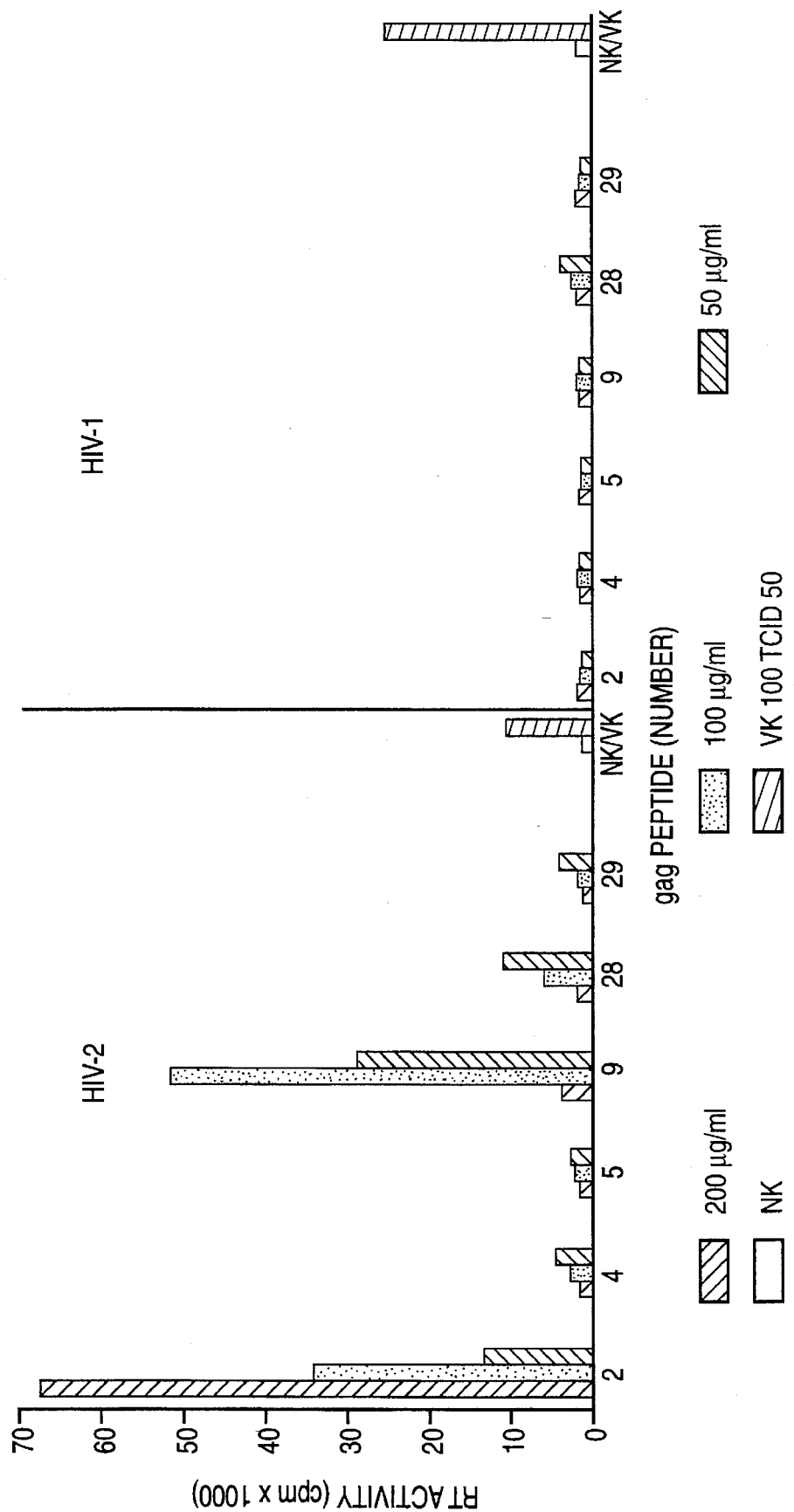
FIG. 3 Inhibition of HIV synthesis by gag peptides (Experiment 3). 100 $TCID_{50}$ HIV-1 and HIV-2 were employed to infect the jurkat and H9 cells respectively. Reverse transcriptase activity measured in cpm in the cell culture supernatant from the detector cell culture. The supernatant was concentrated five-fold by PEG precipitation. VC=virus control; NC=negative control. Twice the NC value was used to exclude negative cell cultures. To improve clarity, the RT values are reported in the figure in logarithmic presentation.
Figure 4A:
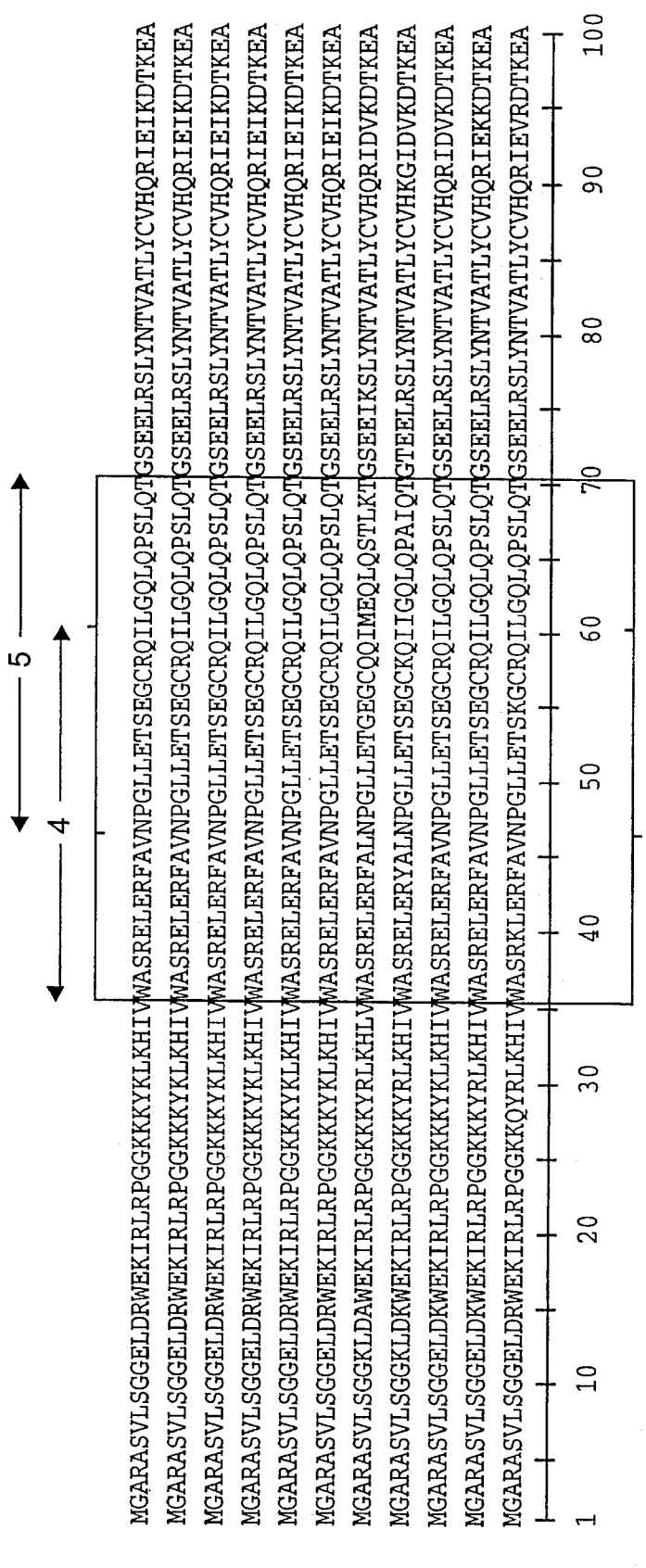
FIGS. 4A, 4B, 5A and 5B: Comparison of various HIV gag protein sequences. The regions represented by peptides 4, 5 and 28, 29 are marked by boxes.
Figure 4B:
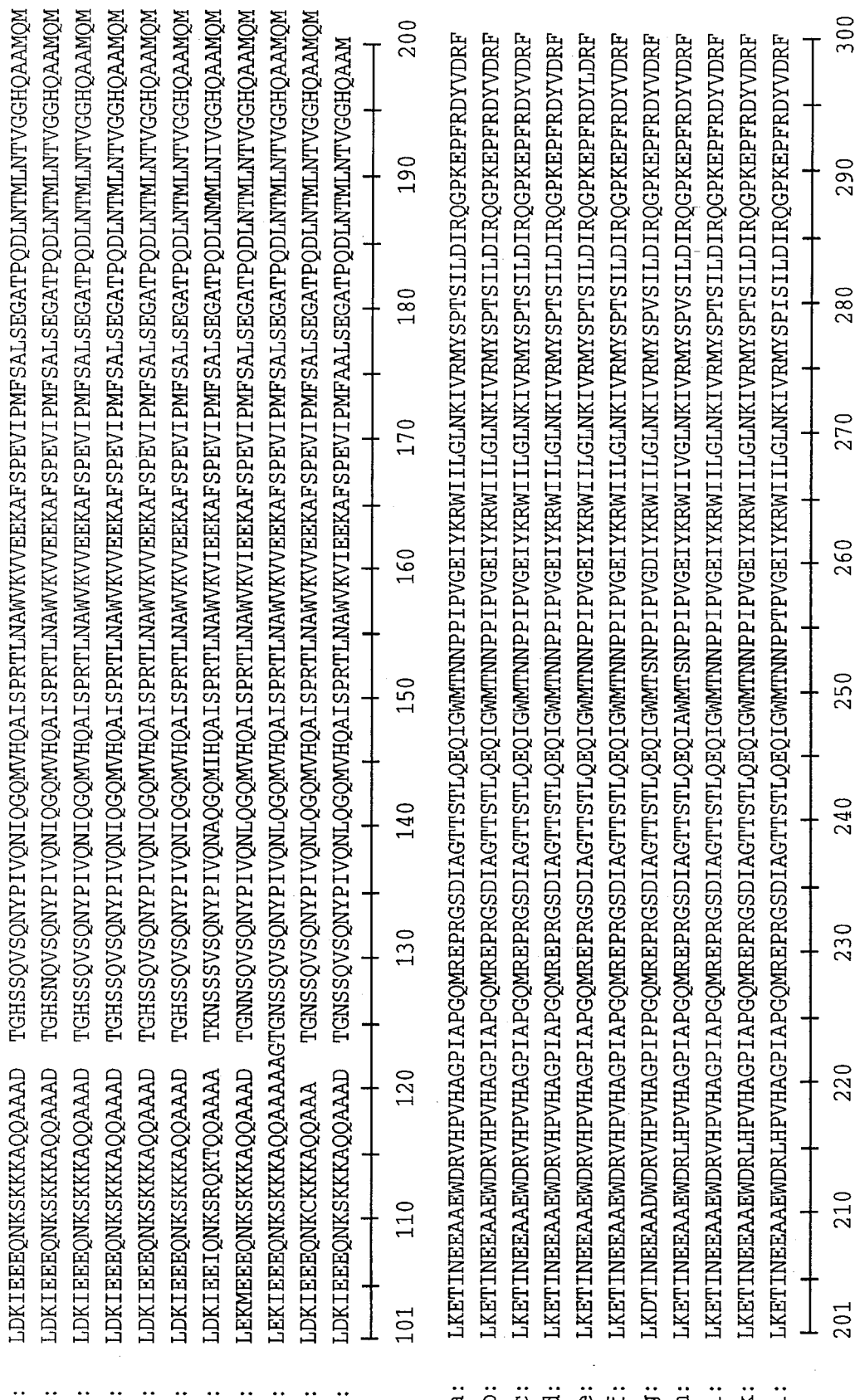
Figure 5A:
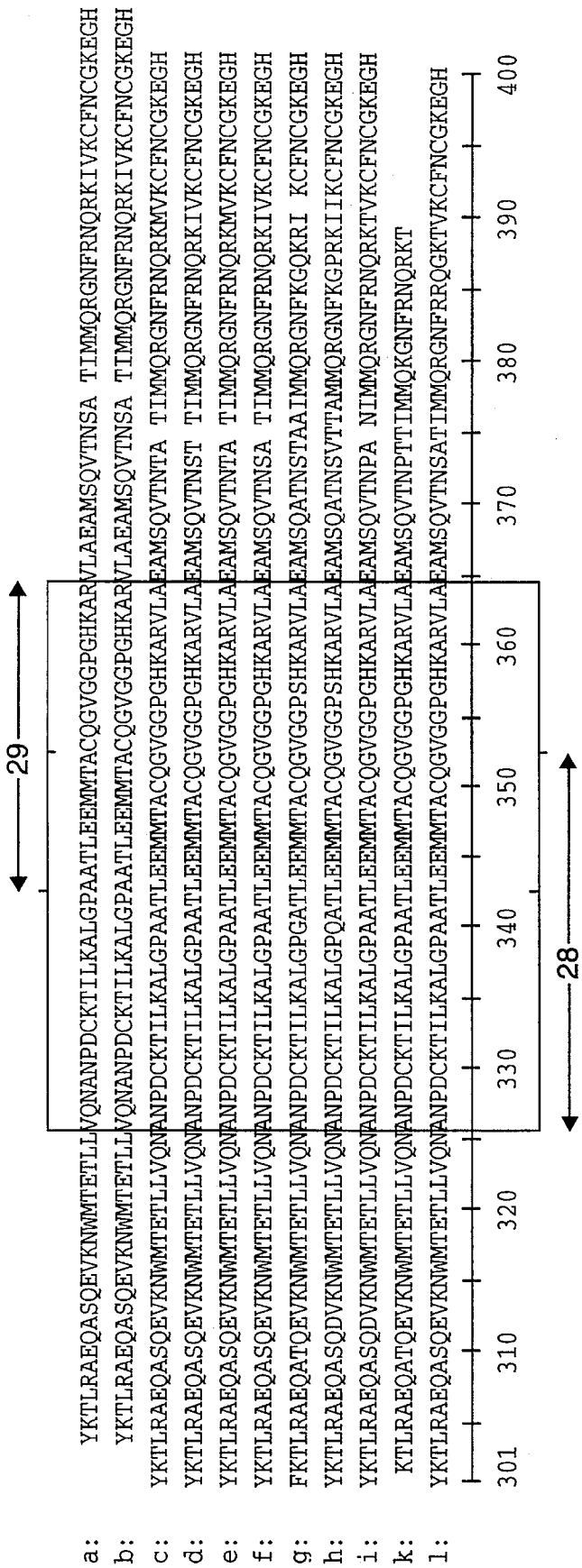
Figure 5B:
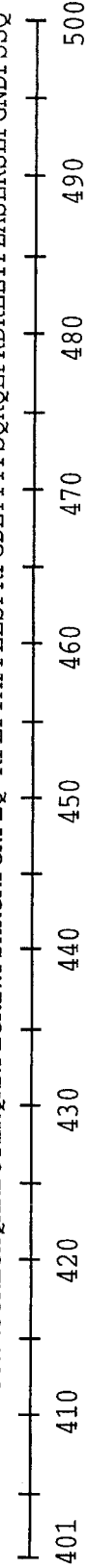
Figure 6A:
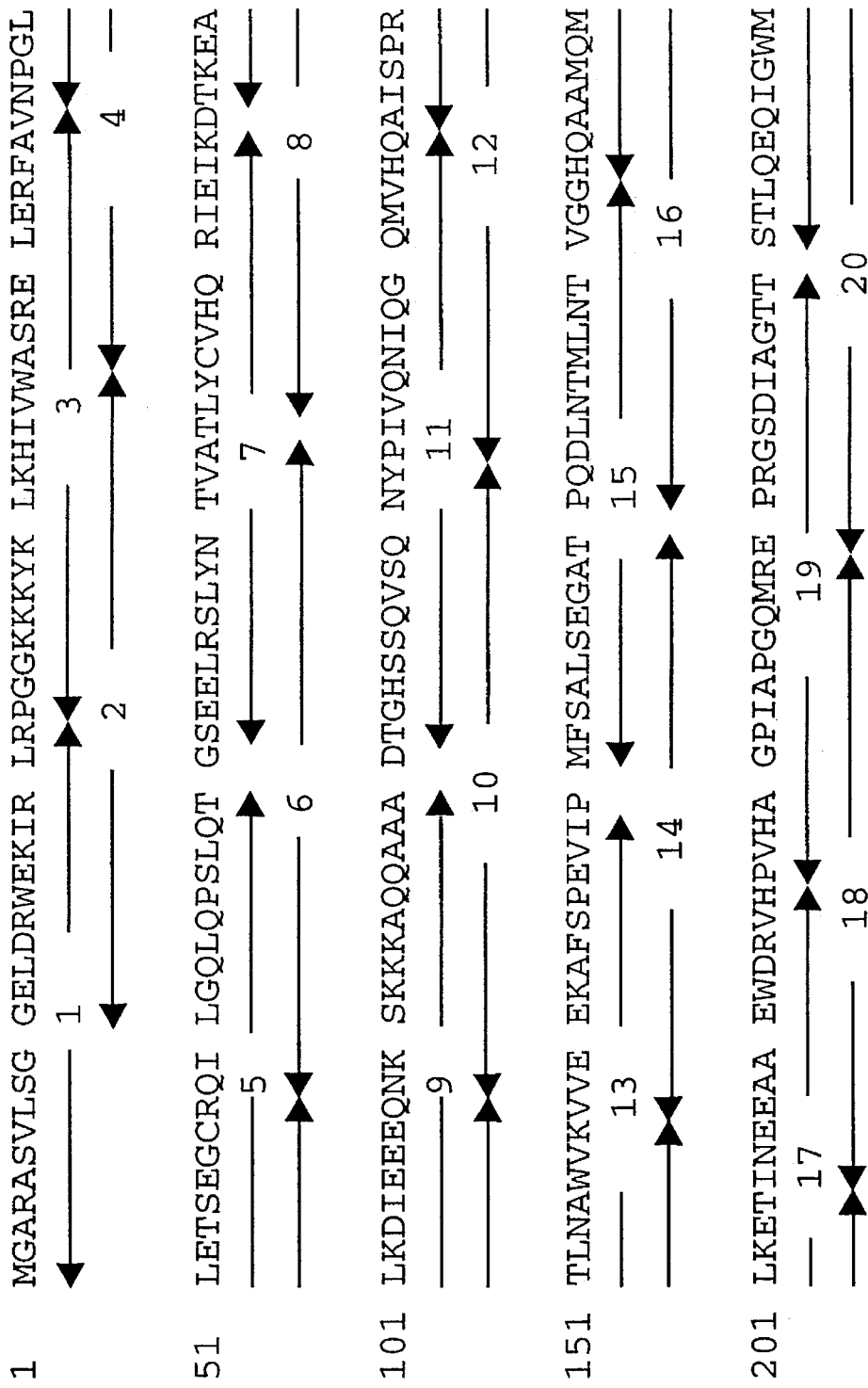
FIGS. 6A and 6B: Amino-acid sequence of the 41 mutually overlapping synthetic gag peptides. The peptides were synthesized in analogy to the sequence published by Ratner et al.
Figure 6B:
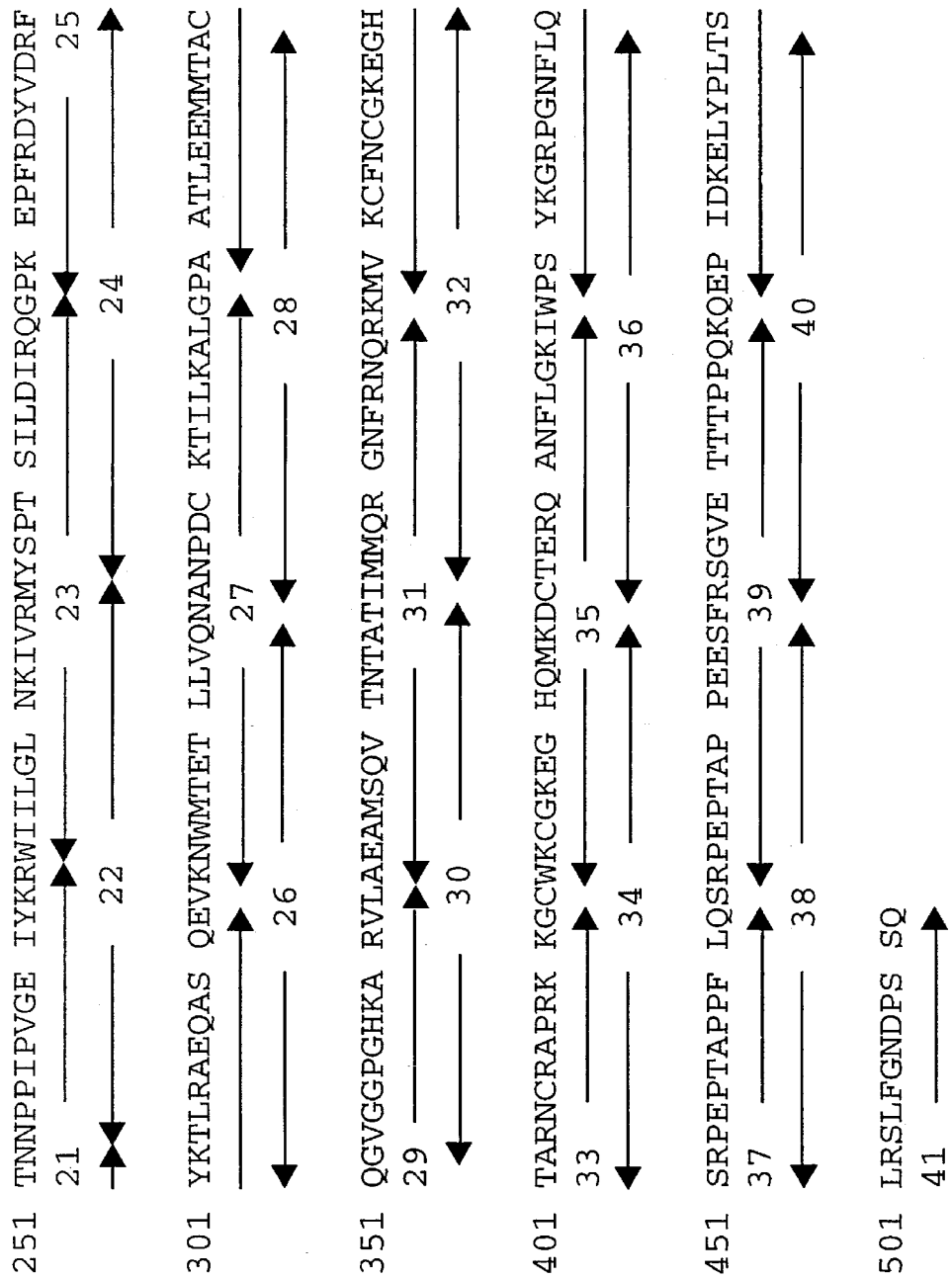
Figure 7:
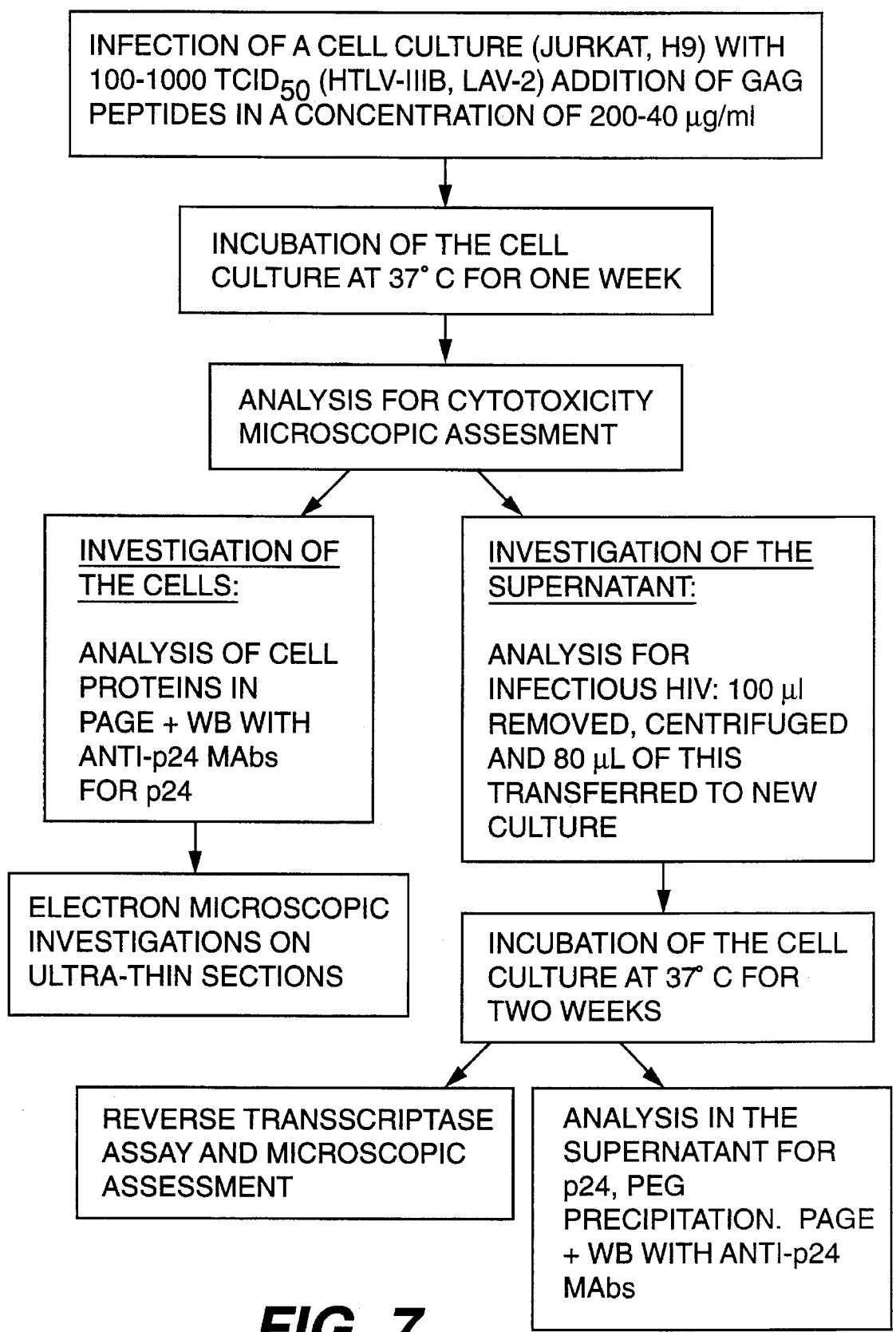
FIG. 7: Diagrammatic experimental design of the experiments carried out and planned to demonstrate the inhibition of HIV virus synthesis with gag peptides.

Inhibition of HIV virus synthesis with gag peptides:

| Peptide No.: | p24 Detection: |
| --- | --- |
| 1 | + |
| 2 | + |
| 3 | + |
| 4 | – |
| 5 | (+) |
| 6 | ++ |
| 7 | ++ |
| 8 | ++ |
| 9 | + |
| 10 | + |
| 11 | + |
| 12 | + |
| 13 | + |
| 14 | + |
| 15 | + |
| 16 | + |
| 17 | + |
| 18 | ++ |
| 19 | + |
| 20 | + |
| 21 | + |
| 22 | + |
| 23 | + |
| 24 | + |
| 25 | ++ |
| 26 | ++ |
| 27 | ++ |
| 28 | (+) |
| 29 | – |
| 30 | ++ |
| 31 | + |
| 32 | + |
| 33 | + |
| 34 | ++ |
| 35 | ++ |
| 36 | ++ |
| 37 | + |
| 38 | + |
| 39 | + |
| 40 | + |
| 41 | + |

We claim:
1. A peptide of the HIV gag protein having the amino acid sequence NPGLLETSEGCRQ.

* * * * *